United States Patent [19]

Besozzi et al.

[11] 4,044,067

[45] Aug. 23, 1977

[54] PURIFICATION OF UNSATURATED COMPOUNDS

[75] Inventors: Alfio J. Besozzi; Alan W. Foster, both of Houston, Tex.

[73] Assignee: Petro-Tex Chemical Corporation, Houston, Tex.

[21] Appl. No.: 627,117

[22] Filed: Oct. 30, 1975

Related U.S. Application Data

[60] Division of Ser. No. 420,046, Nov. 29, 1973, abandoned, which is a continuation-in-part of Ser. No. 223,363, Feb. 3, 1972, abandoned.

[51] Int. Cl.$^2$ .................. C07C 11/12; C07C 15/00; C07C 11/00; C07C 7/00
[52] U.S. Cl. .................. 260/680 E; 260/669 A; 260/677 A; 260/681.5 R; 260/683 R; 260/683.3
[58] Field of Search .................. 423/245; 260/669 A, 260/677 A, 680 E, 681.5 R, 683 R, 683.3

[56] References Cited

U.S. PATENT DOCUMENTS

| 3,437,703 | 4/1969 | Reitmeier et al. | 260/680 E |
|---|---|---|---|
| 3,557,238 | 1/1971 | Cunningham | 260/680 E |
| 3,607,966 | 9/1971 | Croce | 260/680 E |
| 3,801,669 | 4/1974 | Christmann | 260/680 E |
| 3,925,498 | 12/1975 | Stadig | 260/683.3 |

*Primary Examiner*—O. R. Vertiz
*Assistant Examiner*—Brian E. Hearn
*Attorney, Agent, or Firm*—Kenneth H. Johnson; N. Elton Dry

[57] ABSTRACT

Gaseous streams containing carbonyl compounds are reduced in carbonyl compounds by reacting a vapor phase with catalyst comprising as the major cation portion at least two metals of Periodic Table Groups 1b, 2b, 4b, 6b, 7b and 8. Reactor effluent from oxidative dehydrogenation reaction to produce butadiene-1,3 is reacted with iron oxide - copper chromite on AMC catalyst to remove carbonyl compounds.

1 Claim, No Drawings

PURIFICATION OF UNSATURATED COMPOUNDS

This is a division of application Ser. No. 420,046, filed Nov. 29, 1973, now abandoned, which is a continuation-in-part of Ser. No. 223,363 filed Feb. 3, 1972, now abandoned.

This application relates to a process for the reduction in carbonyl impurities in gaseous streams. A preferred embodiment relates to a process for the purification of unsaturated hydrocarbons from a gaseous mixture containing hydrocarbons, relatively non-condensable gases and carbonyl compounds as an impurity.

Unsaturated hydrocarbons are commercially produced by the catalytic dehydrogenation of more saturated hydrocarbons. For example, diolefins are produced in large quantities by the dehydrogenation of saturated hydrocarbons or olefins.

Improved processes for the preparation of unsaturated hydrocarbons such as butene, butadiene-1,3 isoprene and styrene are processes whereby hydrocarbons such as butane, butene, isopentenes or ethyl benzene are dehydrogenated at elevated temperatures in the presence of catalysts and oxygen and such processes are known as oxidative dehydrogenation processes. Superior results and yields of product are thereby obtained. However, the product streams contain not only the desired unsaturated hydrocarbon, but also various oxygenated compounds such as aldehydes and other carbonyl compounds. When air is used as the source of the oxygen, the effluent from the dehydrogenation reactor will contain large quantities of relatively non-condensable gases, such as nitrogen. The gaseous effluent may also contain varying amounts of steam. It is one of the principal objects of this invention to provide a process for the separation of the carbonyl and other oxygenated compounds from the gaseous stream containing hydrocarbons.

The oxygenated compounds are a serious contaminant in the unsaturated hydrocarbon product and must be essentially completely removed in order to have a product of suitable purity, e.g., a product having on the order of a few parts per million carbonyl compounds. The essentially complete removal of the oxygenated compound is quite difficult for several reasons. In the first place, the oxygenated compounds constitute only a very minor percentage of the gaseous stream to be purified. Normally the carbonyl compounds will constitute less than 5 mol percent of the gaseous stream to be purified and more usually may constitute such as less than or up to 2.5 mol percent of the gaseous stream. Generally the feed stream will contain at least about 10 ppm carbonyl compounds based on the other organic compounds such as the hydrocarbons. The oxygenated compounds are therefore quite difficult to remove because of their low concentrations in the gaseous stream. In addition, the oxygenated compounds may be difficult to separate from compounds such as hydrocarbons regardless of their relative concentration. Azeotropes may form between the oxygenated compounds and various hydrocarbons. For instance, an azeotrope is formed between acetaldehyde and butadiene-1,3. It is therefore an object of this invention to promote a process for the removal of carbonyl compounds from a gaseous stream containing only minute quantities of carbonyl compounds based on the total gaseous stream.

Prior processes have dealt with the separation of oxygenated compounds from oxidative dehydrogenation processes. In U.S. Pat. Nos. 3,308,201 and 3,336,414 oxygenated compounds are removed by scrubbing with an aqueous composition. These processes have the drawback that the carbonyl compounds are transferred to a scrubbing water and must still be disposed of such as by biodegradation. According to U.S. Pat. No. 3,557,238 the carbonyl compounds are condensed with the steam from the reactor effluent, revaporized and fed back to the dehydrogenation reactor. Therefore, one object of this invention is to provide a process for the destruction of carbonyl compounds. It is a further object to destroy the carbonyl compounds without significantly losing reactor product or significantly isomerizing any of the products. It is also an object to produce a catalyst which has long catalyst life and which has a reduced tendency to form coke. Another object is to provide a process which is particularly effective in destroying formaldehyde because formaldehyde is difficult to economically separate from aqueous compositions.

According to this invention is has been discovered that mixtures of the elements and compounds thereof of Periodic Table* Groups 1b, 2b, 4b, 6b, 7b and 8 catalyze the destruction of oxygenated compounds in vapor phase. Thus, it is possible to contact the reactor effluent directly with a catalyst bed and destroy oxygenated compounds.

*All references in this application are to the Periodic Table as found on page B-3 of the 51st. edition of the Handbook of Chemistry & Physics (1970-71 Chemical Rubber Publishing Company).

In general mixtures of atoms of metals of the Periodic Table Groups 1b, 2b, 4b, 6b, 7b and 8 are effective in the process of this invention. The atoms may be present such as in the form of the metal compounds such as oxides, salts or hydroxides. Many of these metals, salts and hydroxides may change during the preparation of the catalyst, during heating in a reactor prior to use in the process of this invention, or are converted to another form under the described reaction conditions, but such materials still function as an effective catalyst in the defined process to give carbonyl removal or destruction. For example, the metal may be present as the nitrates, nitriles, carbonates, hydroxides, acetates, sulfites, silicates, sultides and the like. For instance, iron nitrate and iron sulfate may be converted at least to some extent to the corresponding oxides while being heated in a reactor to a reaction temperature of about 550° C. Such salts of the defined metal groups, which are normally stable at the defined reaction temperatures may likewise be effective under the conditions of the described reaction. However, some metal compounds are more effective than other compounds of the same metal and, therefore, the compound giving the most effective results can be chosen. Preferably, catalysts solid under the conditions of carbonyl removal will be used. Preferably, the compound will exhibit some basicity e.g. as in the case of oxides, carbonates or hydroxides. It has been found that prior art compositions that are known as thermal or oxidative dehydrogenation catalysts or as hydrogenation catalysts have been effective to destroy carbonyl compounds according to this invention.

Examples of preferred catalysts are mixtures of Ti, Zr, Cr, Mn, Cu, Zn, Pd, Pt, Co and Fe, and more preferably mixtures of Zr, Cr, Mn, Cu, Zn and Fe. In the Periodic Table Group 8 elements Fe and the platinum group metals are preferred with Fe being particularly preferred. The term mixtures thereof includes compounds thereof such as the ferrites. Useful compounds include, for example, cupric bromide, cuprous chloride, cuprous oxide, cupric oxide, cuprous silicide, cuprous sulfide, cupric phosphate, silver oxide, zinc fluoride, zinc oxide, zinc ortho phosphate, zinc phosphide, zinc orthosilicate, zinc metasilicate, zinc sulfide, cadmium oxide, titanium dioxide, zirconium oxide, $CrBr_2$, $Cr_2O_3$, manganese dioxide, manganese disilicide, ferrous oxide, ferric oxide and $Fe_3O_4$. The platinum metal elements are the elements of the Fifth and Sixth Periods of Group 8 of the Periodic Table. These elements are ruthenium, rhodium, palladium, osmium, iridium, platinum. Preferred catalysts are platinum, palladium, compounds thereof, and mixtures of these. Suitable catalysts are such as palladium metal, palladium monoxide, platinum oxide(ous), platinum metal, platinum-rhodium alloys and the like. The mixture of elements of Groups 1b, 2b, 4b, 6b, 7b and 8 are the main active constituents of the catalyst. Aluminum can be present in fairly large amounts but the exact function of aluminum is not known as aluminum by itself does not particularly catalyze the reaction. Non metals such as silica can be present. Oxides, hydroxides, or carbonates under the conditions of reaction to destroy the carbonyl compounds are preferred. Ingredients or anions which suppress or deactivate the effect of the defined metal elements should be avoided.

Good results have been obtained with catalysts containing transition elements of the Periodic Table as the predominant metals.

Particularly preferred catalysts according to the present invention comprise as the major cation component at least two members from different Periodic Table Groups selected from the group consisting of elements of Periodic Table Groups 1b, 2b, 4b, 6b, 7b and 8. The preferred elements are Ti, Zr, Cr, Mn, Cu, Zn, Pd, Pt, Co and Fe and, furthermore, preferred elements are Zr, Cr, Mn, Cu, Zn and Fe. A preferred catalyst is one consisting of mixtures of Zr, Cr, Mn, Cu, Zn or Fe, wherein one member is Mn.

A preferred type of catalyst is one which comprises iron and especially preferred are those that comprise iron as the major metal or cation component by weight. Another preferred catalyst is Fe and Zn. The iron and other compounds can be present as oxides or other compounds or may be present as e.g. hydroxides, carbonates, nitrates, acetates, etc. One form is as ferrites such as manganese ferrite, zinc ferrite, zinc chromium ferrite, mixtures thereof and the like. The ferrites may contain more than one metal as illustrated. Methods of preparing ferrites are disclosed, e.g. in U.S. Pat. Nos. 3,284,536; 3,270,080; 3,303,235; 3,334,152; 3,342,890; 3,526,675 and so forth. Mixtures of iron oxide with other compounds such as oxides have given excellent results. Thus, iron can be combined as a compound or other combination such as a ferrite or as a mixture of compounds with at least one metal from the Group 4b metals such as Ti, Group 6b metals such as Cr, Group 7b metals such as Mn, Group 8 metals such as Co, Group 1b metals such as Cu, Group 2b metals such as Zn. Additionally, e.g. Al, Si, P, Bi may be present. Examples of mixtures of iron oxide with other compounds may be found in U.S. Pat. Nos. 2,461,147 and 3,308,193.

The catalysts of this invention may be used as such or may be coated on catalyst carriers. Catalyst carriers are known in the art and include such compounds as alumina, silica, silicon carbide and so forth. Diluents may also be incorporated into the catalyst so long as the diluent does not prevent the catalyst from functioning. Preferably the carrier should be low surface and low acidity.

The gaseous mixture to be treated containing the carbonyl* compounds as an impurity may be obtained from a variety of sources. However, the invention is particularly suitable for the purification of gaseous effluents resulting from the oxidative dehydrogenation of organic compounds including hydrocarbons utilizing air or oxygen diluted with non-condensable diluents such as nitrogen or helium. Examples of oxidative dehydrogenation processes are disclosed, e.g. in U.S. Pat. Nos. 3,207,805; 3,284,536; 3,320,329; 3,342,890; and 3,476,824.

*All references to overall quantities of carbonyl compounds are determined by ASTM Method D-1089 and reported as acetaldehyde. The procedure is modified to exclude the analysis of acetals. Generally, the carbonyl compounds will have from 1 to 8 carbon atoms, e.g. from 1 to 6 carbon atoms when a $C_4$ to $C_6$ compound is being dehydrogenated, and will have from 1 to 2 carbonyl groups. Formaldehyde is included in this definition.

Organic compounds to be dehydrogenated may be acyclic, cycloaliphatic or alkyl aryl compounds of 3 or 4 to 9 carbon atoms, which contain at least two adjacent carbon atoms, each of which carbon atom has at least one hydrogen atom attached. Olefins, diolefins or compounds may be produced from more saturated compounds e.g. butadiene-1,3 may be produced from n-butane. A mixture of monoolefins and diolefins may also be produced such as a mixture of butadiene-1,3 and butenes from a feedstock of a mixture of n-butane and butene. Cyclohexane may be dehydrogenated to cyclohexene and/or benzene. Ethyl benzene or ethyl cyclohexane may be dehydrogenated to styrene. Good results may be obtained with an organic feed containing at least 50, such as at least 75 mol percent of an acyclic aliphatic hydrocarbon. Hydrocarbons of 4 to 5 carbon atoms having a straight chain of at least four carbon atoms, e.g., those having a single double bond have been used and preferred are the monoethylenically unsaturated compounds or mixtures of saturated and monoethylenically unsaturated compounds. Hydrocarbons having from 4 to 8 carbon atoms constitute a preferred feed with n-butane, n-butene, isopentane, isopentene, ethyl benzene and mixtures having given excellent results.

Oxygen will generally be supplied to the dehydrogenation zone in the range of about 0.20 mol of oxygen to 2.0 to 3.0 mols of oxygen per mol of hydrocarbon to be dehydrogenated. A preferred range for the oxygen is from about 0.3 to 1.50 mols of oxygen per mol of hydrocarbon to be dehydrogenated. Either air, oxygen or oxygen diluted with a diluent such as nitrogen, helium, and the like, may be utilized. The oxygen may be supplied in gaseous form or via a solid oxygen carrier such as in U.S. Pat. No. 3,420,911. Steam may be fed to the dehydrogenation zone in amounts such as from about 2 to 40 mols of steam per mol of hydrocarbon to be dehydrogenated. An advantageous range is from 2 to 20 mols of steam per mol of hydrocarbon.

The dehydrogenation reaction may be conducted in the absence of contact catalysts, but better results are obtained if the reaction is conducted in the presence of metal or metal compound catalysts. The dehydrogenation reactor may be a fixed or fluid bed reactor. Reactors conventionally used for the dehydrogenation of hydrocarbons to butadiene may be employed. The total pressure in the dehydrogenation zone may suitably be about atmospheric pressure. However, higher pressures or vacuum may be used. Pressures such as from about atmospheric (or below) up to about 100 to 200 p.s.i.g. may be employed. The dehydrogenation reaction will normally be conducted at a temperature at least about 250° C. such as greater than about 300° or 375° C. and the maximum temperature in the reactor may be about 700° or 800° C. or perhaps higher such as 900° C.

The effluent from the dehydrogenation zone will contain the impure unsaturated organic products, various impurities including oxygenated hydrocarbons, noncondensable* gases and perhaps some unconverted feed, oxygen and steam. If air is used as the source of oxygen, nitrogen will be present in relatively large quantities as a noncondensable gas. Steam may be present in an amount up to 96 mol percent of the total effluent, such as from about 5 to 96 percent. On a water free basis the organic phase including dehydrogenated product, any unreacted feed, oxygenated hydrocarbons, polymer and tar and precursors thereof and any organic decomposition products usually range from about 1 to 50 mol percent of the effluent and generally will be within the range of or about 3 to 30 mol percent of the effluent. Also on a water free basis the noncondensable gases, such as nitrogen or $CO_2$, will usually be present in an amount of from or about 20 to 93 mol percent of the total effluent, but more often will be within the range of about 40 to 80 mol percent.

*The term "noncondensable" or "inert noncondensable" gases refers to those gases, other than hydrocarbons, such as nitrogen, $CO_2$ and CO, which do not condense under the conditions encountered.

In those uses wherein the effluent stream passing over the decarbonylation catalyst is deficient in oxygen, particularly less than 1 mole percent of the reactor effluent, the water gas reaction becomes an important consideration and some steam becomes essential to the successful operation of the catalyst in a commercial manner. If the effluent stream is derived from an oxidative dehydrogenation steam will normally be a usual constituent of the effluent stream in sufficient quantities, i.e., 3 to 30 mols of steam per mol of total organic compound (for example, unsaturated hydrocarbon and carbonyls).

The effluent gases leaving the dehydrogenation zone will generally be at a temperature of at least 400° or 450° C. with suitable ranges being between 450° or 500° C. and 800° or 900° C. depending upon the particular dehydrogenation process. According to the preferred embodiment of this invention the gases are fed directly into the catalyst bed for the destruction of oxygenated compounds or at least are fed to the catalyst bed prior to condensation of steam from the effluent gases. This catalyst bed may be incorporated into the same reactor chamber as the dehydrogenation bed, e.g., packing material may optionally be added between the dehydrogenation catalyst and the carbonyl destruction catalyst. Generally, the reactor effluent will not cool appreciably before the carbonyl destruction catalyst is encountered and, therefore, the temperature will be within the same ranges as for the reactor effluent. Optionally, prior to contacting with the carbonyl destruction catalyst the gaseous feed may be cooled or heated to give an optimum temperature for carbonyl destruction without adversely affecting the product. Also it is within the scope of the invention to remove portions or components of the reactor effluent prior to contacting with the catalyst. Normally the composition fed to the carbonyl destruction catalyst will contain at least 3 or 5 mols of uncondensed steam per mol of total organic compound such as hydrocarbon and may contain e.g. from 3 to 30 mols of steam. The reactor effluent will generally contain less than 5 mol percent free oxygen and may initially contain less than one mol percent of the reactor effluent. It is possible to add oxygen to the reactor effluent prior to contacting with the carbonyl destruction catalyst such as adding e.g. up to five mols of oxygen per mol of carbonyl compound but care should be exercised to avoid the explosive limits.

The presence of oxygen can be very detrimental in that the present decarbonylation catalyst tend to completely oxidize the unsaturated compound, e.g., hydrocarbon products. Hence, although oxygen can help keep the decarbonylation catalyst from coking, it may do so at the sacrifice of unsaturated product. For this reason, the present invention is carried out with less than 5 mol and preferably less than 1 mol percent free oxygen present in the feed passing over the present catalyst.

The gaseous composition to be fed to the carbonyl destruction catalyst zone will preferably comprise, exclusive of any water present, about or from 3.5 to 80 mol percent of unsaturated hydrocarbon, about or from 0.005 to 2.5 mol percent of carbonyl compounds, and about or from 20 to 93 mol percent of noncondensable gases (i.e. noncondensable under the conditions of contact with the catalyst) all based on the total mols of gaseous composition being fed to the catalyst.

After the catalyst has been used for a period of time it may be regenerated such as by oxidation with air and/or with steam. Procedures for the regeneration of dehydrogenation catalysts to remove coke may be employed.

The following examples are only illustrative and are not intended to limit the invention. All percentages are by weight unless expressed otherwise.

EXAMPLES 1 - 4

A series of runs is made to illustrate the effect of certain catalysts on the destruction of carbonyl compounds in an effluent stream containing unsaturated hydrocarbons. In each instance 25 cc of catalyst of 6 to 8 mesh (U.S. Standard) is employed in a 1 inch Vycor reactor. The reactor temperature is controlled within the range of 555° to 575° C. The feed to the reactor is a mixture of 6 ml/min. of liquid carbonyl mixture of 0.3% by weight of 50% - 50% by weight mixture of formaldehyde and acetaldehyde which is vaporized by passing through a steam generator, 930 ml/min of gaseous nitrogen, and 575 ml/min of gaseous butadiene-1,3 with the gaseous volumes being calculated at 760 mm and 0° C. In the runs in which $CO_2$ is also added the carbonyl mixture is still fed at a rate of 6 ml per minute but the nitrogen is 720 ml/min, the butadiene-1,3 is 575 ml/min and the $CO_2$ is 210 ml/min. In all of these feeds steam is present in an amount of 13 mols per mol of hydrocarbon. The contact time of the feed with the catalyst is about 0.05 seconds. The percent removal of carbonyl compounds is analyzed by the hydroxylamine HCL method, calculated on feed and effluent as $CH_3CHO$ (Reference Analytical Chem. Vol. 23, 1758). In the runs where a carrier is employed the percent carrier is the percent by weight based on the total weight of carrier and actives. The alumina carrier is an aluminum oxide carrier type AMC of 6 to 8 mesh (U.S. Standard). The ingredients in the catalyst are by weight percent. The $CO_2$ is added in some runs to simulate this adverse condition of the feed. Sampling is started after 30 minutes in order to give the catalyst a chance to equilibrate. The product is then collected for a period of 80 minutes and the collected sample is analyzed for percent carbonyl removal.

| Example | Catalyst, wt. % | Carrier, wt. % | $CO_2$ Present | % Carbonyl Removal |
|---|---|---|---|---|
| 1 | 33.6 ZnO, 1.4 $Cu_3(PO_4)_2$ | 65 alumina | No | 14 |
| 2 | Quartz chips | — | No | 0 |
| 3 | SAS 350 $Al_2O_3$ | | No | 0 |
| 4 | 14.4 ZnO, 3.9 $MnO_2$, 16.8 $Cr_2O_3$[1] | 65 alumina | No | 42 |

[1]Catalyst of Example 5 prepared by precipitation from combining $ZnSO_4 \cdot 7H_2O$ + $MnSO_4 \cdot H_2O$ and $(NH_4)_2CrO_4$ solutions. Calcined at 400° C. for 4 hours.

results of an 80 minute sample and in all examples the catalyst is first run for 30 minutes for equilibration.

| Ex. | Catalyst Composition, wt. % | Carrier wt. % | % Carbonyl Removal |
|---|---|---|---|
| 5 | 97 Zinc ferrite - $3H_3PO_4$ impregnated with $Cr_2O_3$[1] | | 85 |
| 6 | ZnO, CuO (Girdler G-GGB) | | 34 |
| 7 | 30 $ZnCrFeO_4$[1] (ferrite) | 70 alumina | 6, 41 (successive run) |
| 8 | 33 Nickel ferrite | 67 alumina | coked |

FOOTNOTES for Examples 5 to 8.
[1]Catalyst is prereduced with a mixture of steam and hydrogen for 3 hours at 560° C.

| Example | Catalyst Composition, Wt. % | % Aldehyde Destruction[1] | Remarks |
|---|---|---|---|
| 9 | 28.23% $Fe_2O_3$ — 21.77% $ZrO_2$/AMC | 72, 44 | Equal amounts of acetone + acetaldehyde in first sample |
| 10 | 22.3 $Fe_2O_3$ — 11.0 $CuCr_2O_4$/AMC | 55 | $CH_3CHO$. No acetone. |
| 11 | $CuO \cdot CuCr_2O_4$ (Davison 933)/AMC | 69, 82, 89, 90 | Little $CH_3CHO$. Decreasing acetone. |
| 12 | $CuCr_2O_4$/AMC | 85, 69/77, 63 | Increasing $CH_3CHO$. Little or no acetone. |

[1]Values indicated represent successive samples.
[2]Qualitative characterization of residual carbonyls, acetone is produced during the carbonyl destruction.

EXAMPLES 5 to 12

A series of runs is made feeding a mixture of:

| | ml/min. |
|---|---|
| aldehyde solution (50/50 mixture of HCHO and $CH_3CHO$) | 6 |
| nitrogen | 726 |
| butadiene-1,3 | 575 |
| $CO_2$ | 210 |

25cc of 6 – 8 mesh of the respective catalyst are employed. Examples 11 and 12 are the results of a sample taken for 40 minutes and the remaining examples are the

The invention claimed is:
1. In a vapor phase process for the preparation of unsaturated hydrocarbons comprising catalytic oxidative dehydrogenation of a feed stream of hydrocarbon compounds having 4 to 8 carbon atoms to produce an unsaturated hydrocarbon product stream having a greater degree of ethylenic unsaturation than said feed stream and containing organic carbonyl compounds as an impurity wherein the improvement comprises contacting said product stream in vapor phase at a temperature in the range of 250° to 800° C and containing less than 5 mol percent free oxygen with a solid catalyst for destroying said carbonyl compounds consisting of mixtures of oxides of Mn, Zn and Cr, and removing organic carbonyl compounds.

* * * * *